(12) United States Patent
Jensen (10) Patent No.: US 9,149,368 B1
(45) Date of Patent: Oct. 6, 2015

(54) SPONDYLOLITHESIS REDUCTION SPINAL INSERT FUSION CAGE AND METHOD OF REDUCING SPONDYLOLITHESIS

(71) Applicant: Wade K. Jensen, Dakota Dunes, SD (US)

(72) Inventor: Wade K. Jensen, Dakota Dunes, SD (US)

( * ) Notice: Subject to any disclaimer, the term of this patent is extended or adjusted under 35 U.S.C. 154(b) by 302 days.

(21) Appl. No.: 13/840,126

(22) Filed: Mar. 15, 2013

(51) Int. Cl.
*A61F 2/44* (2006.01)
(52) U.S. Cl.
CPC ...................... *A61F 2/447* (2013.01)
(58) Field of Classification Search
CPC .............................. A61F 2/4455; A61F 2/447
See application file for complete search history.

(56) References Cited

U.S. PATENT DOCUMENTS

| | | | | |
|---|---|---|---|---|
| 8,556,975 B2* | 10/2013 | Ciupik et al. | ............... | 623/17.15 |
| 2005/0234555 A1* | 10/2005 | Sutton et al. | ............... | 623/17.15 |
| 2008/0033440 A1* | 2/2008 | Moskowitz et al. | ............ | 606/72 |
| 2012/0071978 A1* | 3/2012 | Suedkamp et al. | ........ | 623/17.16 |
| 2015/0081021 A1* | 3/2015 | Ciupik | ....................... | 623/17.15 |

* cited by examiner

*Primary Examiner* — Nicholas Woodall
*Assistant Examiner* — Olivia C Chang (57) ABSTRACT

A spondylolithesis reduction spinal insert fusion cage reduces spondylolithesis. The cage includes a first beam and a second beam each abutting one of a pair of adjacently positioned vertebral bodies. Spaced bars extend from the first beam and a threaded drive shaft is rotatably coupled to the first beam extending between the spaced bars. A second perimeter rim extends from the second beam. The bars are inserted into sleeves extending between the second beam and the second perimeter rim. At least one bridge extending between the sleeves has a medial section engaging the shaft wherein the bridge is moved along the shaft when the shaft is rotated. Each of a pair of connectors couples an associated one of the first beam and the second beam to an associated one of the vertebral bodies.

11 Claims, 10 Drawing Sheets

| Pelvic Incidence (degrees) | Total Lumbar Lordosis Applied (degrees) | Applied Between L1/L2 (degrees) | Applied Between L2/L3 (degrees) | Applied Between L3/L4 (degrees) | Applied Between L4/L5 (degrees) | Applied Between L5/S1 (degrees) |
|---|---|---|---|---|---|---|
| 35 | 45 | 5 | 5 | 5 | 15 | 15 |
| 40 | 50 | 5.5 | 5.5 | 5.5 | 17 | 17 |
| 45 | 55 | 6 | 6 | 6 | 18 | 18 |
| 50 | 60 | 7 | 7 | 7 | 20 | 20 |
| 55 | 65 | 7.5 | 7.5 | 7.5 | 22 | 22 |
| 60 | 70 | 8 | 8 | 8 | 23 | 23 |
| 65 | 75 | 8.5 | 8.5 | 8.5 | 25 | 25 |
| 70 | 80 | 9 | 9 | 9 | 27 | 27 |
| 75 | 85 | 9.5 | 9.5 | 9.5 | 28.3 | 28.3 |
| 80 | 90 | 10 | 10 | 10 | 30 | 30 |
| 85 | 95 | 10.5 | 10.5 | 10.5 | 32 | 32 |
| 90 | 100 | 11 | 11 | 11 | 33 | 33 |

SPONDYLOLITHESIS REDUCTION SPINAL INSERT FUSION CAGE AND METHOD OF REDUCING SPONDYLOLITHESIS

BACKGROUND OF THE DISCLOSURE

Field of the Disclosure

The disclosure relates to spinal insert fusion devices and more particularly pertains to a new spinal insert fusion device for reducing spondylolithesis.

SUMMARY OF THE DISCLOSURE

An embodiment of the disclosure meets the needs presented above by generally comprising a first beam having a surface abutting one of a pair of adjacently positioned vertebral bodies. A pair of spaced bars extend from the first beam and a threaded drive shaft is rotatably coupled to the first beam extending between the spaced bars. A second beam has a surface abutting a second of the pair of vertebral bodies. A second perimeter rim is coupled to and extends from the second beam and abuts the second vertebral body. Each of a pair of sleeves extends between the second beam and a distal section of the second perimeter rim relative to the second beam and is slidably inserted into an associated one of the sleeves to slidably couple the first beam to the second beam. At least one bridge extends between the sleeves having a medial section engaging the shaft wherein the bridge is moved along the shaft when the shaft is rotated. Each of a pair of connectors couples an associated one of the first beam and the second beam to an associated one of the vertebral bodies.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

With reference now to the drawings, and in particular to FIGS. 1 through 13 thereof, a new spinal insert fusion device embodying the principles and concepts of an embodiment of the disclosure and generally designated by the reference numeral 10 will be described.

As best illustrated in FIGS. 1 through 13, the spondylolithesis reduction spinal insert fusion cage 10 generally comprises a first beam 12 having a surface 14 configured for abutting a first opposed surface 16 of a pair of adjacently positioned vertebral bodies 18,20. A pair of spaced bars 22 is coupled to and extends from the first beam 12. A threaded drive shaft 24 is rotatably coupled to the first beam 12. The threaded drive shaft 24 extends from the first beam 12 between the spaced bars 22. A head 26 is coupled to the threaded drive shaft 24. A cavity 28 extends into the head 26 wherein the head 26 is configured for being engaged by a driving tool inserted into the cavity 28. The cavity 28 may have a geometric pattern complimentary to a drive end of the driving tool to facilitate secure insertion of the drive end into the cavity 28 and control of rotation of the drive shaft 24 by turning the drive tool. The above structure may define a lower section 30 of the cage 10 coupled to the lower vertebral body 18. A first perimeter rim 200 may be coupled to and extend from the first beam 12. The first perimeter rim 200 has a surface 202 configured for abutting the first opposed surface 16 of the pair of adjacently positioned vertebral bodies 18,20. The pair of spaced bars 22 may be coupled to and extends between the first beam 12 and a distal section 204 of the first perimeter rim 200 relative to said first beam 12. The first perimeter rim 200 is an elongated strip of material having opposite ends 206 coupled to opposite ends 208 of the first beam 12 forming an opening 210 with the first beam 12 facilitating bone grafting to further secure the cage 10.

A second beam 32 has a surface 34 configured for abutting a second opposed surface 34 of the pair of adjacently positioned vertebral bodies 18,20. As shown, the second opposed surface 34 is on the upper vertebral body 20. A second perimeter rim 36 is coupled to and extends from the second beam 32. The second perimeter rim 36 has a surface 38 configured for abutting the second opposed surface 34 of the pair of adjacently positioned vertebral bodies 18,20. The second perimeter rim 36 is an elongated strip of material having opposite ends 42 coupled to opposite ends 44 of the second beam 32 forming an opening 40 with the second beam 32. A pair of sleeves 46 is coupled to and extends between the second beam 32 and a distal section 48 of the second perimeter rim 36 relative to the second beam 32. Each of the spaced bars 22 is slidably inserted into an associated one of the sleeves 46 wherein the first beam 12 is slidably coupled to the second beam 32 in a plane defined by opposed surfaces 212, 214 of first beam 12, first perimeter rim 200, second beam 32, and second perimeter rim 36. A plurality of bridges 50 are coupled to and extend between the sleeves 46. Each bridge 50 has opposite end sections 52 and a medial section 54 extending between the opposite end sections 52. Each end section 52 of each bridge 50 is arcuate and statically coupled to an associated one of the sleeves 46. The medial section 54 has an arcuate lower edge 56 engaging the threaded drive shaft 24. The arcuate lower edge 56 is held against the drive shaft 24 when the bars 22 are inserted into the sleeves 46. Thus, each bridge 50 is moved along a length of the shaft 24 when the shaft 24 is rotated and the first beam 12 is moved relative to the second beam 32. There may be a single bridge 50 extending between the sleeves 46 or a plurality of bridges 50 arranged in spaced relationship along the sleeves 46. The structure including the second beam 32, second perimeter rim 36, sleeves 46 and bridges 50 may define an upper section 60 of the cage 10. However, the upper section 60 and lower section 30 may also be used in an inverted position. The sleeves 46 or bars 22 may be skewed relative to the opposed surfaces 212,214 as needed to permit the planar alignment as the upper section 60 slides relative to the lower section 30.

A pair of connectors 58 is provided for securing the first beam 12 and second beam 32 to the vertebral bodies 18,20. Each connector 58 couples an associated one of the first beam 12 and the second beam 32 to the associated one of the vertebral bodies 18,20. Each connector 58 may be an elongated substantially triangular blade 62. Each blade 62 is arcuate extending from a base side 64 of the blade 62 to a distal point 66 relative to the base side 64. A plurality of barbs 68 are positioned along opposite side edges 70 extending from the distal point 66 of each blade 62 toward the base side 64. Thus, each blade 62 is configured for setting within a respective one of the vertebral bodies 18,20 such that the first beam 12 and the second beam 32 are fixed to the vertebral bodies 18,20. Therefore, rotation of the shaft 24 after fixing the first beam 12 and second beam 32 to the vertebral bodies 18,20 will urge the vertebral bodies 18,20 to move relative to each other. Rotation of the drive shaft 24 provides smooth fine adjustment of the first beam 12 relative to the second beam 32. The cage 10 includes a pair of connection apertures 84. Each connection aperture 84 extends through an associated one of the first beam 12 and the second beam 32. Each connector 58 extends through an associated one of the connection apertures 84. Each connection aperture 84 is an elongated slit 86 extending through the associated one of the first beam 12 and the second beam 32. Alternatively, each connection aperture 84 may be round and each connector 58 may be a screw inserted through the associated connection aperture 84 securing the first beam 12 and second beam 32 to the vertebral bodies 18,20.

Figure 1:
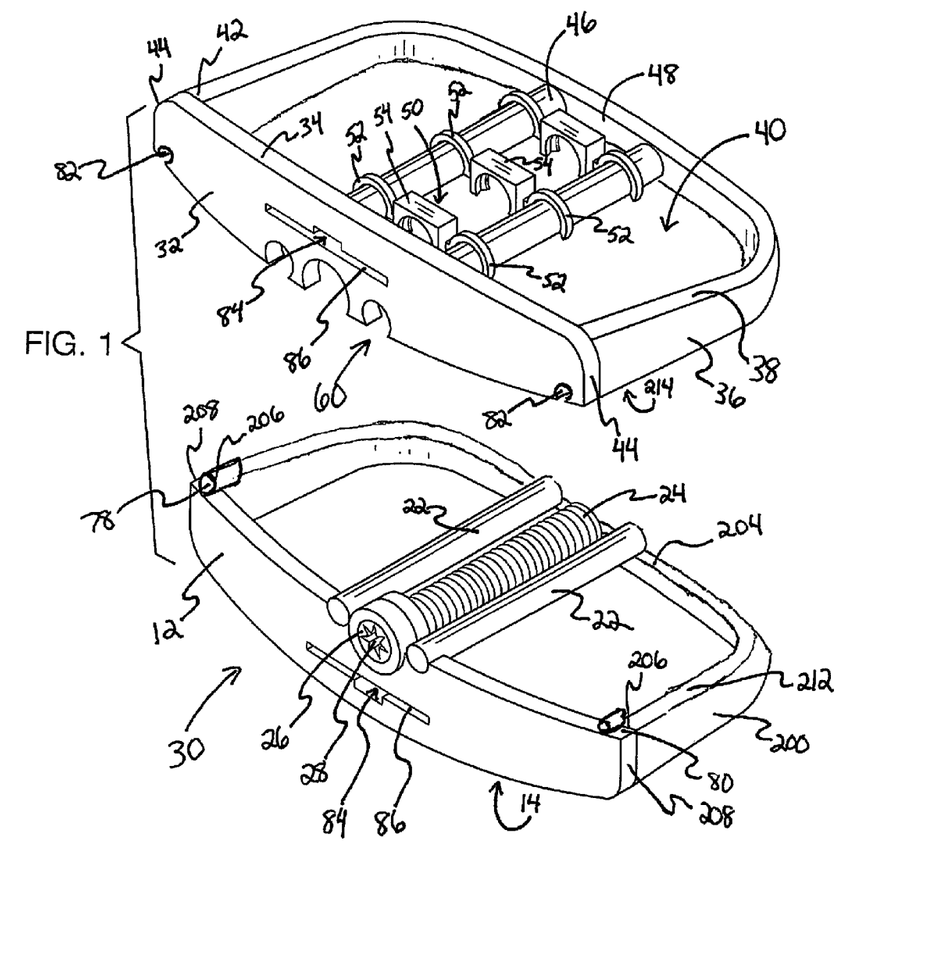
FIG. 1 is a partially exploded top front side perspective view of a spondylolithesis reduction spinal insert fusion cage and method of reducing spondylolithesis according to an embodiment of the disclosure.
Figure 2:
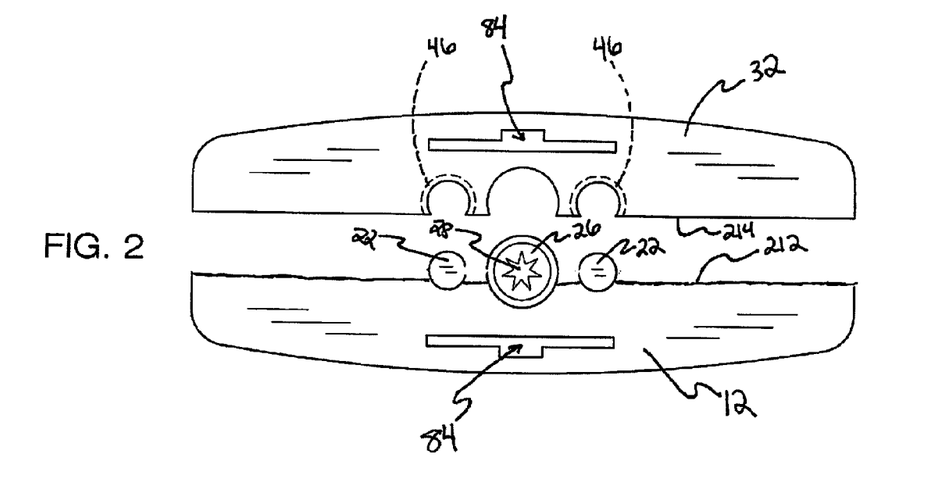
FIG. 2 is a top view of an upper section of an embodiment of the disclosure.
Figure 3:
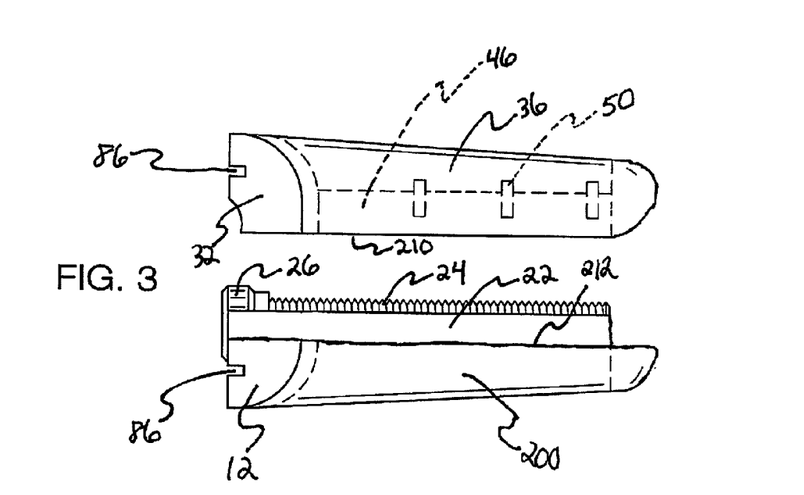
FIG. 3 is a top view of a lower section of an embodiment of the disclosure.
Figure 4:
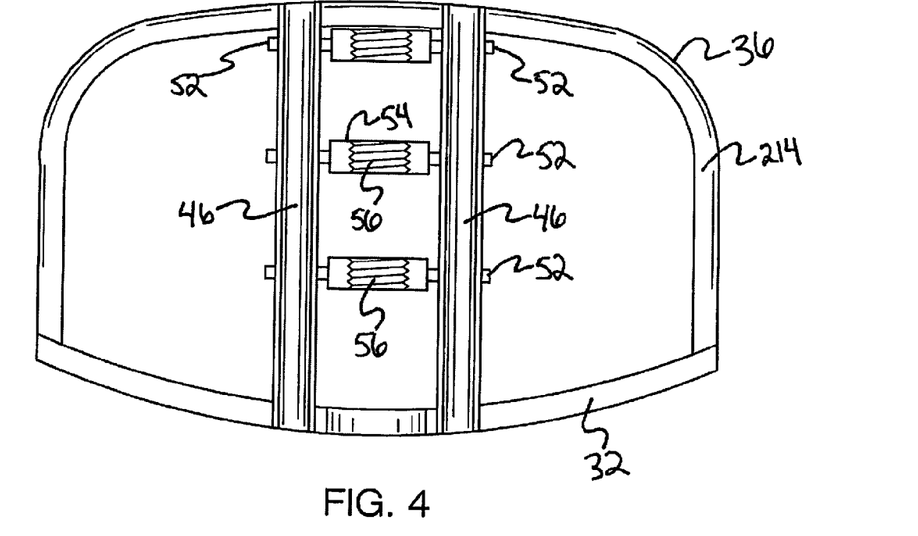
FIG. 4 is a side view of an embodiment of the disclosure.
Figure 5:
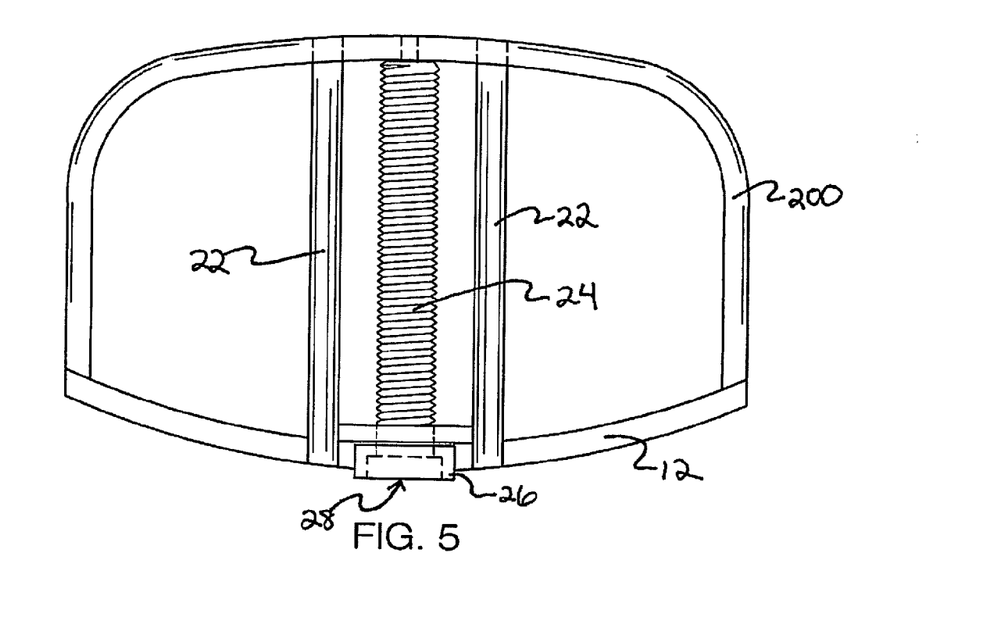
FIG. 5 is a bottom view of an embodiment of the disclosure.
Figure 6:
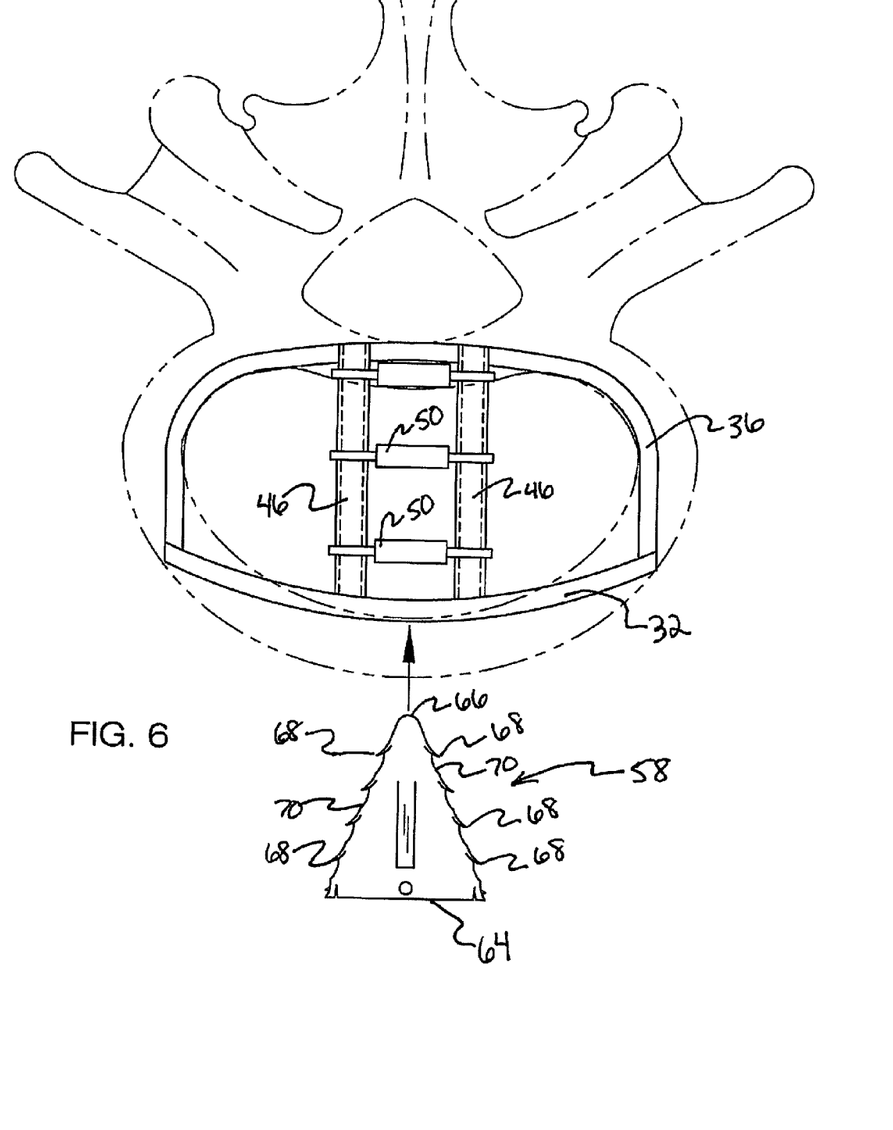
FIG. 6 is a front view of an embodiment of the disclosure.
Figure 7:
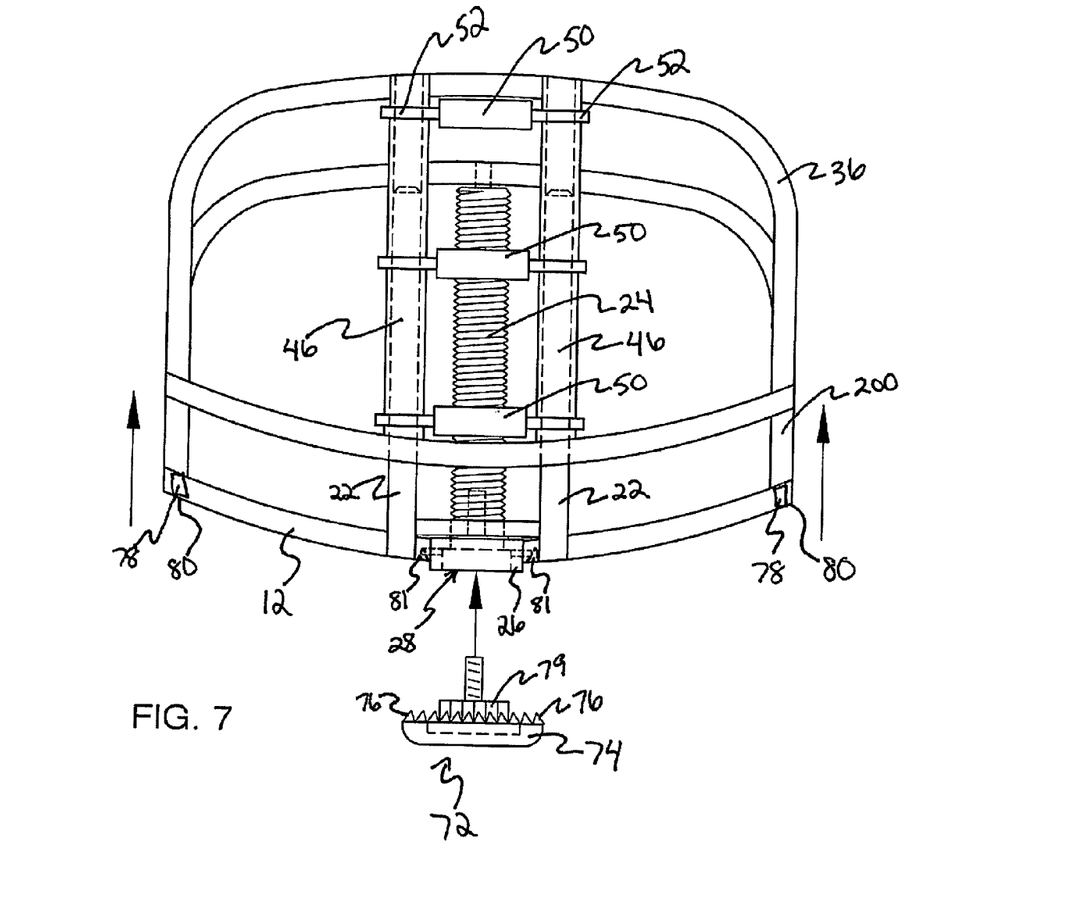
FIG. 7 is a detailed partially exploded top view of a locking mechanism of an embodiment of the disclosure.
Figure 8:
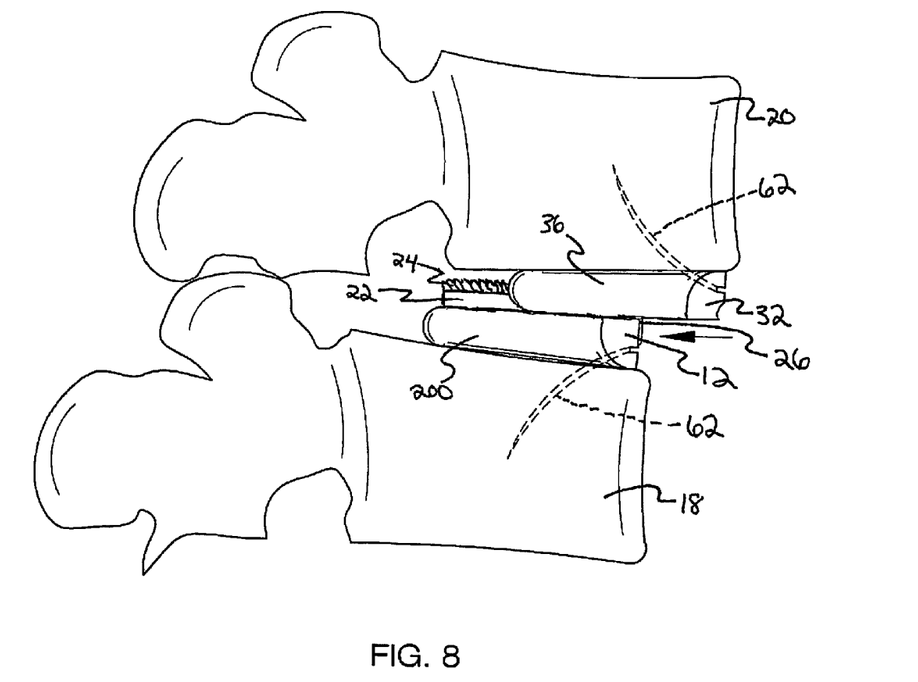
FIG. 8 is a side view of an embodiment of the disclosure in an unreduced spondylolithesis condition.
Figure 9:
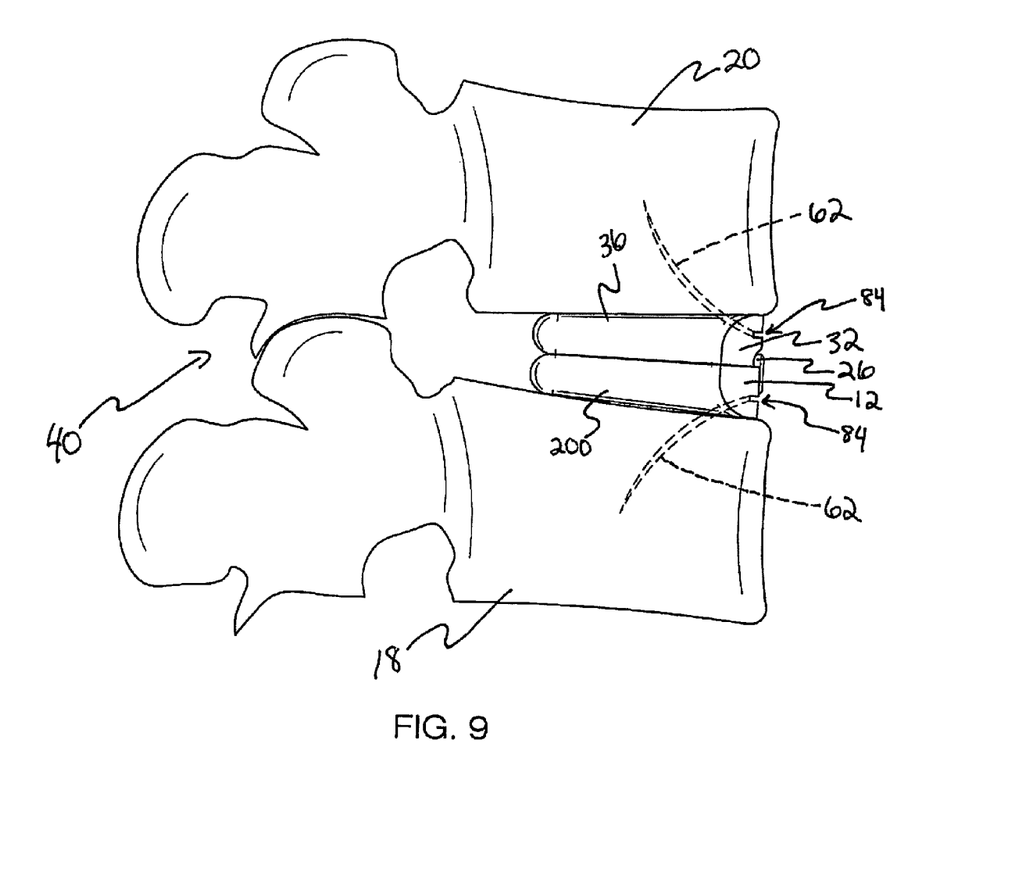
FIG. 9 is a side view of an embodiment of the disclosure in a reduced condition.

A locking mechanism 72 is selectively couplable to the threaded drive shaft 24 and the first beam 12 wherein the locking mechanism 72 restricts rotation of the threaded drive shaft 24 when the locking mechanism 72 engages the threaded drive shaft 24 and the first beam 12. The locking mechanism 72 may be a plate 74 having a projection fitting the cavity 28 and a plurality of teeth 76. The teeth 76 may engage complimentary depressions in the first beam 12 adjacent to the head 26.

A pair of guides 78 may be coupled to and extend from the first beam 12. Each of the guides 78 may be coupled to an associated end 80 of the first beam 12 projecting rearwardly to engage a pair of grooves 82 extending into the second beam 32 when the first beam 12 and second beam 32 are urged into alignment by rotation of the drive shaft 24. The cross-sectional shape of each guide 78 may be complimentary to the shape of the grooves 82. Each of the guides 78 is slidably insertable into an associated one of the grooves 82 when the first beam 12 is coupled to the second beam 32 and urged into alignment. Each of the grooves 82 is positioned adjacent to an associated end 44 of the second beam 32. Thus, the guides 78 and grooves 82 stabilize the upper section 60 relative to the lower section 60.

Figure 10:
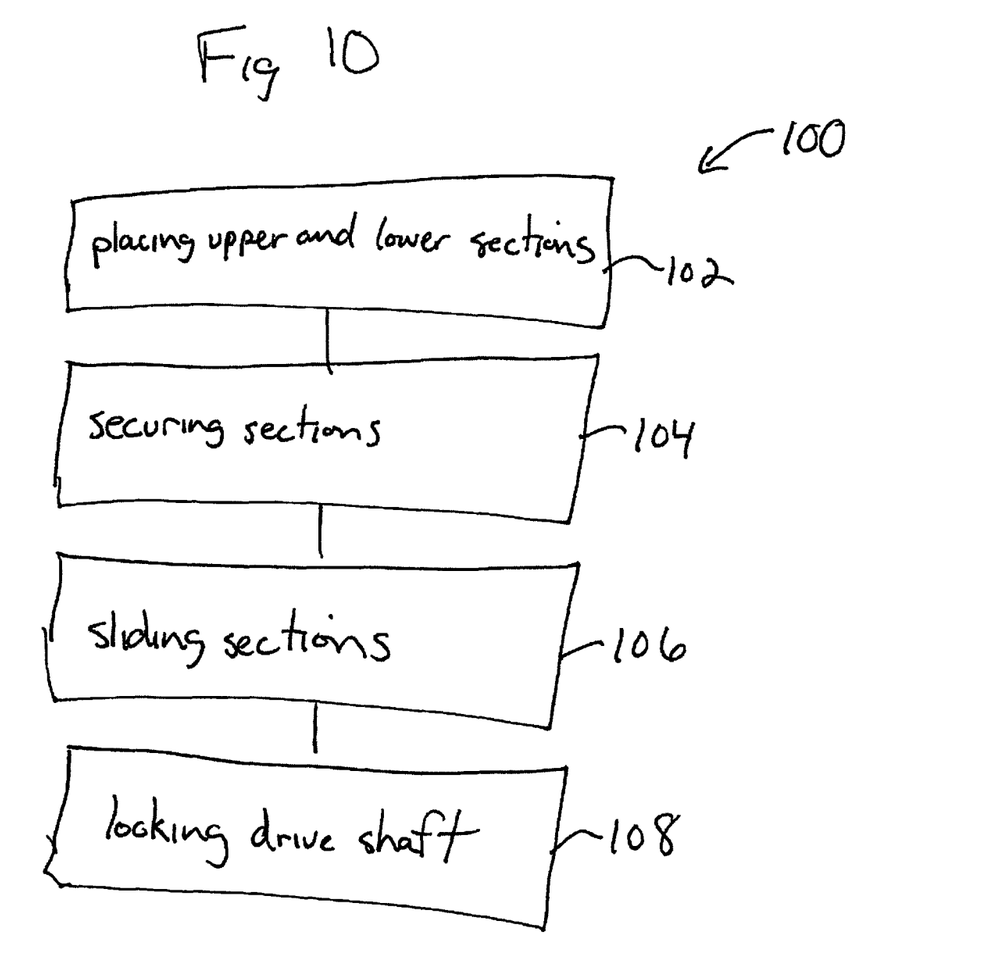
FIG. 10 is a schematic view of a method according to an embodiment of the disclosure.

In use, the cage 10 provides for a method 100 of reducing spondylolithesis. The method 100 includes a step 102 of placing or positioning the upper section 60 and the lower section 30 of the cage 10 described above between the pair of adjacent vertebral bodies 18,20. An additional step 104 is securing the upper section 60 and the lower section 30 to the pair of adjacent vertebral bodies 18,20. The upper section 60 is slidably coupled to the lower section 30 along a line of displacement of the pair of adjacent vertebral bodies 18,20. Another step 106 is sliding the upper section 60 relative to the lower section 30 wherein spondylolithesis is reduced. The upper section 60 is urged to move relative to the lower section 30 by rotating the drive shaft 24 coupled to the lower section 30 and engaging the upper section 60. As may be readily apparent and described above, the cage may be utilized in an inverted position in which case the upper section 60 and lower section 30 would reverse positions. Still yet another step 108 is locking the drive shaft 24 to prevent rotation of the drive shaft 24 such that the first beam 12 is fixed relative to the second beam 32 wherein the pair of vertebral bodies 18,20 are held in a position reducing spondylolithesis. Additional grafting may be employed to further secure the cage 10 to the vertebral bodies 18,20 as desired.

The cage 10 may be inserted from an anterior approach with a technique known as an anterior lumbar interbody fusion (ALIF). The goal is to adjust and reduce front to back misalignment known as spondylolithesis. Continuous threading on the drive shaft 24 engaging the bridges 50 allows smooth adjustment reducing stress on and trauma to the vertebral bodies during surgery. The cage 10 further permits a surgeon to select a precise amount of reduction according to experience, personal observation of the vertebral bodies during the surgical procedure, and other factors previously known or immediately observable during surgery. Further, the cage 10 permits reverse rotation of the shaft 24 prior to locking the shaft 24 in place. Thus, the cage 10 permits a surgeon may make a decision on the final positioning of the cage 10 that is best for the patient with reduced risk of catastrophic failure or damage to the vertebral bodies.

In addition, the surface 14 of the first beam 12 and the surface 34 of second beam 32 may be angled relative to each other such that they provide desired lordosis when the cage 10 is positioned between the adjacent vertebral bodies 18,20 in a final position. The relative planes of the surface 14 of the first beam 12 and the surface 34 of the second beam 32 are determined based on the desired end position after the lower section 30 has been adjusted relative to the upper section 60. Multiple lower sections 30 and upper sections 60 may be provided in various incremental angles including zero degrees, four degrees, eight degrees, and twelve degrees of angle relative to a plane in which a selected lower section 30 connects to a selected upper section 60. By choosing a selectable combination of angles for the lower section 30 and upper section 60, the total lordosis provided by the cage 10, i.e. total angle between the surface 14 of the first beam 12 and surface 34 of the second beam 32, may be adjusted between zero and twenty four degrees. The angles for each surface 14,34 relative to the connection plane may also vary in other increments to provide other specific amounts of lordosis.

Thus, the method 100 may also include adjusting an angle between the vertebral bodies 18,20 while reducing spondylolithesis as described above. The method 100 may include adjustment of only one pair of vertebral bodies 18,20 but may also comprise adjusting a cumulative angle between each of multiple pairs of vertebral bodies to adjust alignment of the spine 40 formed by a plurality of vertebral bodies relative to pre-determined reference lines determined from measurements of pelvic incidence. Additional factors may include pelvic tilt and C7 plumb line. Desired angles between each pair of vertebral bodies may be determined according to the chart of FIG. 11. Additional factors for each particular patient may also be taken into account in addition to pelvic incidence, pelvic tilt and C7 plumb line when determining exact lordosis corrections between specific adjacent vertebral bodies.

Figure 11:
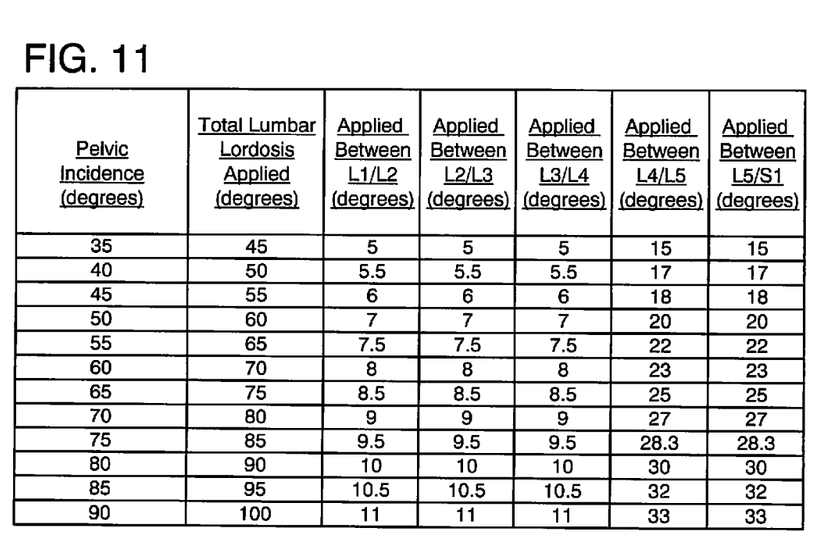
FIG. 11 is a graph of intervertebral spacing between adjacent vertebral endplates to achieve a desired cumulative spinal adjustment.

As shown in FIG. 11, total lumbar lordosis (LL) required is well estimated by the formula LL=pelvic incidence (PI) plus ten (10) degrees, or using a more rigid formula wherein LL=0.56×PI+33. Current practice is for two-thirds of the cumulative lordosis correction to be provided in between the L4/5 and L5/S1 vertebral bodies and the remaining correction divided evenly between L1/2, L2/3, and L3/4 vertebral bodies. These formulas provide a framework for determining the patient's sagittal imbalance that may need correction. Other factors may be included in determining total corrective lordosis if there is a positive sagittal imbalance on standing 36-inch radiographs as determined by the C7 plumb line. For example, a patient with hyper thoracic kyphosis may require additional lumbar lordosis to provide desired results.

Figure 12:
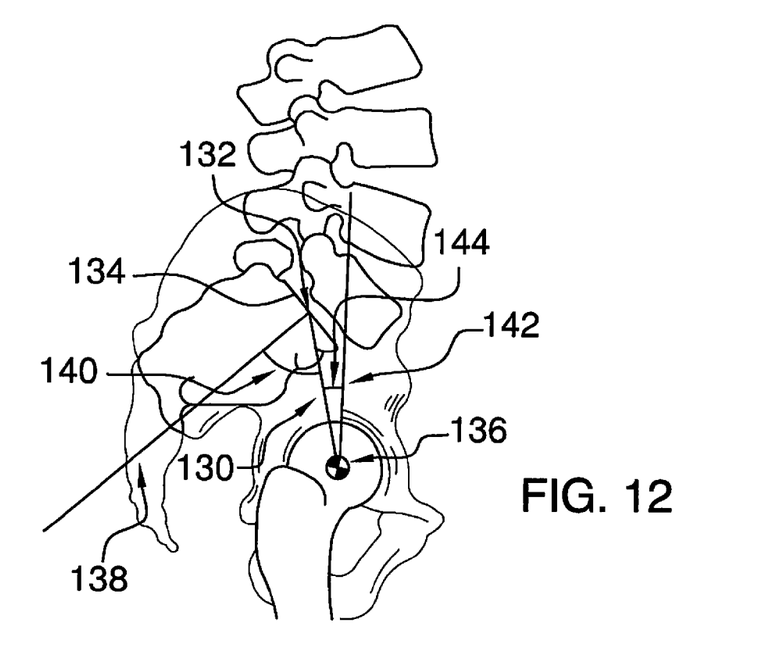
FIG. 12 is side view demonstrating measurement of pelvic incidence.
Figure 13:
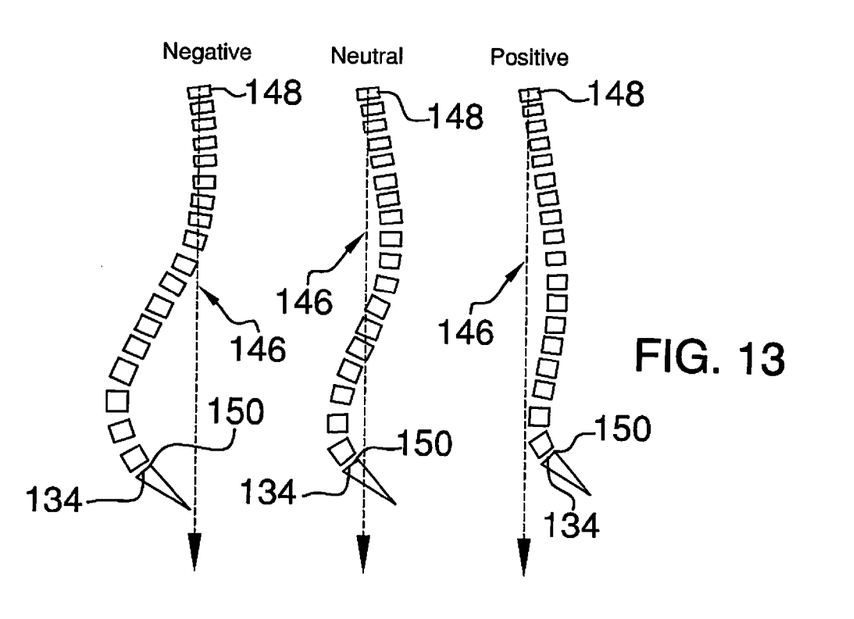
FIG. 13 is a side view demonstrating spinal alignment relative to a C7 plumb line.

As demonstrated in FIG. 12, pelvic incidence is measured by drawing a line 130 from the midpoint 132 of the S1 superior endplate 134 to the center of the midpoint 136 between both femoral heads. A second line 138 is drawn parallel to a perpendicular line from the S1 endplate 134 with the starting point at the midpoint 132 of the S1 superior endplate 134. The angle 140 measured between these two lines 130,138 is the pelvic incidence. This measurement defines the relationship between the spine and the pelvis and can be used to predict the amount of lumbar lordosis needed to maintain a neutral sagittal balance. As also shown in FIG. 12, pelvic tilt is measured using the line 130 from the midpoint 136 between the center of the femoral heads to the midpoint 132 of the S1 superior endplate 134. A vertical reference line 142 is drawn vertically from the midpoint 136 between both femoral heads. An angle 144 created between the line 130 and the vertical reference line 142 represents the pelvic tilt. The angle 144 helps the surgeon determine if the patient is compensating for lack of lumbar lordosis by increasing their pelvic tilt to maintain a neutral sagittal balance. As shown in FIG. 13, C7 plumb line 146 is drawn on a 36 inch lateral radiograph by finding the middle of the C7 vertebral body 148 and drawing a vertical line downward. A measurement from the posterior superior corner 150 of the S1 vertebral endplate 134 to the C7 plumb line 146 is measured. This determines the patient's sagittal balance. A positioning of the C7 plumb line 146 posterior to the superior corner 154 of the S1 endplate is considered a negative sagittal balance, and a positive value is noted when the C7 plumb line 146 is anterior to the posterior superior corner 150 of the S1 vertebral endplate 134. A positive sagittal balance value of greater than 5 centimeters is considered abnormal.

With the above information for a particular patient, incremental adjustment between adjacent vertebral bodies 18,20 may be determined consistent with FIG. 12 and any additional factors deemed necessary to provide the desired total cumulative adjustment of the spine 40 relative to the position of the pelvis 110 to reestablish sagittal balance as opposed to merely straightening the spine 40 and reducing spondylolithesis.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An inter-vertebral spondylolithesis reduction spinal insert cage assembly comprising:
    a first beam having a surface configured for abutting a first opposed surface of a pair of adjacently positioned vertebral bodies;
    a first perimeter rim coupled to and extending from said first beam, said first perimeter rim having a surface configured for abutting the first opposed surface of the pair of adjacently positioned vertebral bodies;
    a pair of spaced bars coupled to and extending between said first beam and a distal section of said first perimeter rim relative to said first beam;
    a threaded drive shaft rotatably coupled to said first beam, said threaded drive shaft extending from said first beam between said spaced bars;
    a second beam having a surface configured for abutting a second opposed surface of the pair of adjacently positioned vertebral bodies;
    a second perimeter rim coupled to and extending from said second beam, said second perimeter rim having a surface configured for abutting the second opposed surface of the pair of adjacently positioned vertebral bodies;
    a pair of sleeves coupled to and extending between said second beam and a distal section of said second perimeter rim relative to said second beam, each of said spaced bars being slidably inserted into an associated one of said sleeves wherein said first beam is slidably coupled to said second beam;
    at least one bridge coupled to and extending between said sleeves, said bridge having opposite ends being statically coupled to an associated one of said sleeves, said bridge having a medial section engaging said threaded drive shaft wherein said bridge is moved along a length of said shaft when said shaft is rotated; and
    a pair of connectors, each connector configured to couple an associated one of said first beam and said second beam to an associated one of the vertebral bodies.

2. The assembly of claim 1, further comprising a plurality of said bridges, said bridges being arranged in spaced relationship along said sleeves.

3. The assembly of claim 1, further comprising:
    a head coupled to said threaded drive shaft; and a cavity extending into said head wherein said head is configured for being engaged by a driving tool inserted into said cavity.

4. The assembly of claim 3, further comprising a locking mechanism selectively couplable to said threaded drive shaft and said first beam wherein said locking mechanism restricts rotation of said threaded drive shaft when said locking mechanism engages said threaded drive shaft and said first beam.

5. The assembly of claim 1, further comprising:
a pair of guides coupled to and extending from said first beam; and
a pair of grooves extending into said second beam, each of said guides being slidably insertable into an associated one of said grooves when said first beam is coupled to said second beam.

6. The assembly of claim 5, further comprising each of said grooves being positioned an associated end of said second beam.

7. The assembly of claim 5, further comprising each of said guides being coupled to an associated end of said first beam.

8. The assembly of claim 1, further comprising a pair of connection apertures, each said connection aperture extending through an associated one of said first beam and said second beam; and
each said connector extending through an associated one of said connection apertures.

9. The assembly of claim 8, further comprising:
each connection aperture being an elongated slit extending through said associated one of said first beam and said second beam; and
each said connector being a substantially triangular blade, each said blade being arcuate extending from a base side of said blade to a distal point relative to said base side.

10. The assembly of claim 9, further comprising a plurality of barbs along opposite side edges extending from said distal point of each said blade.

11. An inter-vertebral spondylolithesis reduction spinal insert cage assembly comprising:
a first beam having a surface configured for abutting a first opposed surface of a pair of adjacently positioned vertebral bodies;
a first perimeter rim coupled to and extending from said first beam, said first perimeter rim having a surface configured for abutting the first opposed surface of the pair of adjacently positioned vertebral bodies;
a pair of spaced bars coupled to and extending between said first beam and a distal section of said first perimeter rim relative to said first beam;
a threaded drive shaft rotatably coupled to said first beam, said threaded drive shaft extending from said first beam between said spaced bars;
a head coupled to said threaded drive shaft;
a cavity extending into said head wherein said head is configured for being engaged by a driving tool inserted into said cavity;
a second beam having a surface configured for abutting a second opposed surface of the pair of adjacently positioned vertebral bodies;
a second perimeter rim coupled to and extending from said second beam, said second perimeter rim having a surface configured for abutting the second opposed surface of the pair of adjacently positioned vertebral bodies;
a pair of sleeves coupled to and extending between said second beam and a distal section of said second perimeter rim relative to said second beam, each of said spaced bars being slidably inserted into an associated one of said sleeves wherein said first beam is slidably coupled to said second beam;
a plurality of bridges coupled to and extending between said sleeves, said bridge having opposite ends being statically coupled to an associated one of said sleeves, said bridge having a medial section engaging said threaded drive shaft wherein said bridge is moved along a length of said shaft when said shaft is rotated, said bridges being arranged in spaced relationship along said sleeves;
a pair of connectors, each connector configured to couple an associated one of said first beam and said second beam to an associated one of the vertebral bodies, each said connector being an elongated substantially triangular blade, each said blade being arcuate extending from a base side of said blade to a distal point relative to said base side;
a plurality of barbs along opposite side edges extending from said distal point of each said blade wherein each said blade is configured for setting within a respective one of the vertebral bodies such that said first beam and said second beam are fixed to said vertebral bodies;
a locking mechanism selectively couplable to said threaded drive shaft and said first beam wherein said locking mechanism restricts rotation of said threaded drive shaft when said locking mechanism engages said threaded drive shaft and said first beam;
a pair of guides coupled to and extending from said first beam, each of said guides being coupled to an associated end of said first beam;
a pair of grooves extending into said second beam, each of said guides being slidably insertable into an associated one of said grooves when said first beam is coupled to said second beam, each of said grooves being positioned an associated end of said second beam; and
a pair of connection apertures, each said connection aperture extending through an associated one of said first beam and said second beam, each said connector extending through an associated one of said connection apertures, each connection aperture being an elongated slit extending through said associated one of said first beam and said second beam.

* * * * *